United States Patent
Termanini

(10) Patent No.: US 9,248,021 B1
(45) Date of Patent: Feb. 2, 2016

(54) MORSE TAPER PROTECTIVE SLEEVE

(71) Applicant: Zafer Termanini, Port Saint Lucie, FL (US)

(72) Inventor: Zafer Termanini, Port Saint Lucie, FL (US)

( * ) Notice: Subject to any disclaimer, the term of this patent is extended or adjusted under 35 U.S.C. 154(b) by 0 days.

(21) Appl. No.: 14/732,753

(22) Filed: Jun. 7, 2015

(51) Int. Cl.
*A61F 2/30* (2006.01)
*A61F 2/36* (2006.01)

(52) U.S. Cl.
CPC ......... *A61F 2/30728* (2013.01); *A61F 2/30721* (2013.01); *A61F 2/3609* (2013.01); *A61F 2/30742* (2013.01); *A61F 2002/30718* (2013.01); *A61F 2002/30917* (2013.01); *A61F 2002/30919* (2013.01); *A61F 2250/006* (2013.01)

(58) Field of Classification Search
CPC .............. A61F 2/3609; A61F 2/30734; A61F 2002/3654; A61F 2/30724; A61F 2/30728; A61F 2002/30729; A61F 2/30742; A61F 2002/30738; A61F 2002/30736; A61F 2002/30682; A61F 2002/30686; A61F 2002/30683; A61F 2002/30917; A61F 2002/30919; A61F 2002/30718
See application file for complete search history.

(56) References Cited

U.S. PATENT DOCUMENTS

| | | | | |
|---|---|---|---|---|
| 6,264,699 | B1 * | 7/2001 | Noiles et al. | 623/23.23 |
| 6,613,092 | B1 * | 9/2003 | Kana et al. | 623/20.15 |
| 6,863,692 | B2 * | 3/2005 | Meulink | 623/23.52 |
| 2004/0087885 | A1 * | 5/2004 | Kawano et al. | 604/8 |

* cited by examiner

Primary Examiner — Matthew F Desanto
(74) Attorney, Agent, or Firm — Samir Termanini

(57) ABSTRACT

A removable orthopedic protective sleeve adapted to be applied over the male Morse taper of modular orthopedic implants thereby preventing contamination of the taper contact surface from blood, body fluid or tissue particles responsible for electrochemical corrosion and fretting at the level of Morse taper. Said sleeve having a conical tube shape and a rim at its upper narrow end. A plurality of vertical grooves situated on the outer surface of the protective sleeve will split open as the female Morse taper of the articular ball is slidingly pushed downward and seated over the male taper. The split sleeve is then removed after the male and female tapers are assembled in-situ.

9 Claims, 4 Drawing Sheets

MORSE TAPER PROTECTIVE SLEEVE

FIELD OF THE INVENTION

The present invention relates to a novel orthopedic protective sleeve adapted to be applied over the male portion of Morse taper of orthopedic joint replacement implant.

BACKGROUND OF THE INVENTION

In the orthopedic field of joint replacement it is quite conventional for implants to have modular components in order to offer the operating surgeon multiple sizes and comply with different anatomy. The operating surgeon assembles said components in the operative wound. Morse taper has been used as easy and strong mechanical mean to assemble different components by simply inserting and impacting the male taper into the female taper. This technique still involves assembly of the components In Situ after insertion of the larger component first.

Moreover, during the component assembly process there is a great risk of contaminating the male and female tapered contact surfaces of the implant with blood and other body fluids as well as tissue particles present n the surgical wound. Said contamination has caused electrochemical corrosion which resulted in local tissue inflammation and osteolysis requiring extensive revision procedures. It has been well known that fluid and materials caught between the contact surfaces of the male and female taper were blamed as cause in initiating the corrosive process and release of metal hydrites.

SUMMARY OF THE INVENTION

The present invention finds application to any orthopedic implant utilizing Morse taper to assemble its components. It serves the purpose of eliminating contamination of the Morse taper contact surfaces by blood and bodily fluid as well as tissue debris present in the surgical field. Such cellular debris and fluid have been implicated in generation of bi-metal electrolytic process and subsequent release of detrimental metallic hydrides leading to local cellular reaction and ultimately osteolysis. More specifically, the invention in its broadest concept relates to a disposable and removable protective sleeve applied over the male taper component of an implantable device.

The general purpose of the present invention, which will be described subsequently in greater details, is to provide a new removable and disposable sleeve to protect the male taper end of an implant during surgical implantation procedure. The new protective sleeve has many advantages, which are not anticipated, rendered obvious, suggested, or even implied by any of the prior art. To attain this, the present invention generally comprises a sleeve having a conical shape and a diameter equal to the implant's male Morse taper and a circular rim situated at the top narrow end of the sleeve. Said rim is firmly attached to the sleeve and has a centered opening at the top end to allow the male Morse taper to slide through. Said circular rim is situated in a horizontal plane and orthogonal to the longitudinal axis of the conical protective sleeve.

In addition, the outer surface of the protective sleeve has a plurality of vertically situated indentation grooves (release slits) allowing the operating surgeon to easily remove the sleeve upon assembly of the male and female components of the Morse Taper. There has thus been outlined, rather broadly, the more important features of the invention in order that the detailed description thereof may be better understood, and in order that the present contribution to the art may be better appreciated.

There are additional features of the invention that will be described hereinafter. In this respect, before explaining at least one embodiment of the invention in detail, it is to be understood that the invention is not limited in its application to the details of the construction and to the arrangement of the components set forth in the following description or illustrated in the drawings.

The invention is capable of other embodiments and of being practiced and carried out in various ways. In example, the protective sleeve can be oval in shape rather than round if the protective sleeve is used with dual taper stems where the male Morse taper has an oval rather than round cross section. Also, it is to be understood that the phraseology and terminology employed herein are for the purpose of the description and should not be regarded as limiting. A primary object of the present invention is to provide a disposable removable protective sleeve that will eliminate contamination of the male Morse taper of an implant thereby elimination the risk of electrochemical and fretting corrosion caused by interposition of blood and tissue debris between the male/female contact surfaces of the taper. Furthermore, the male Morse taper can be covered with a metal catalyst such as Palladium, which reduces corrosive reactions and metal hydrites. The sleeve of this invention will protect the thin metallic film during surgical manipulations and insertions.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated.

BRIEF DESCRIPTION OF THE DRAWINGS

Various other objects, features and attendant advantages of the present invention will become fully appreciated as the same become better understood when considered in conjunction with the accompanying drawings, in which like reference characters designate the same or similar parts throughout the several views, and wherein.

DETAILED DESCRIPTION OF THE INVENTION

Figure 1:
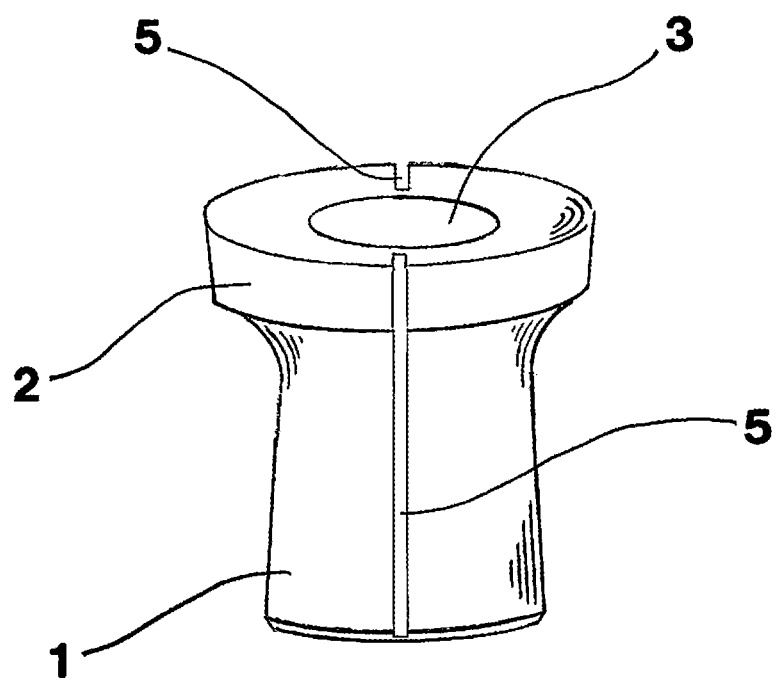
FIG. 1 is a perspective view of the protective sleeve.

Turning now descriptively to the drawings, in which similar reference characters denote similar elements throughout the several views.

Figure 2:
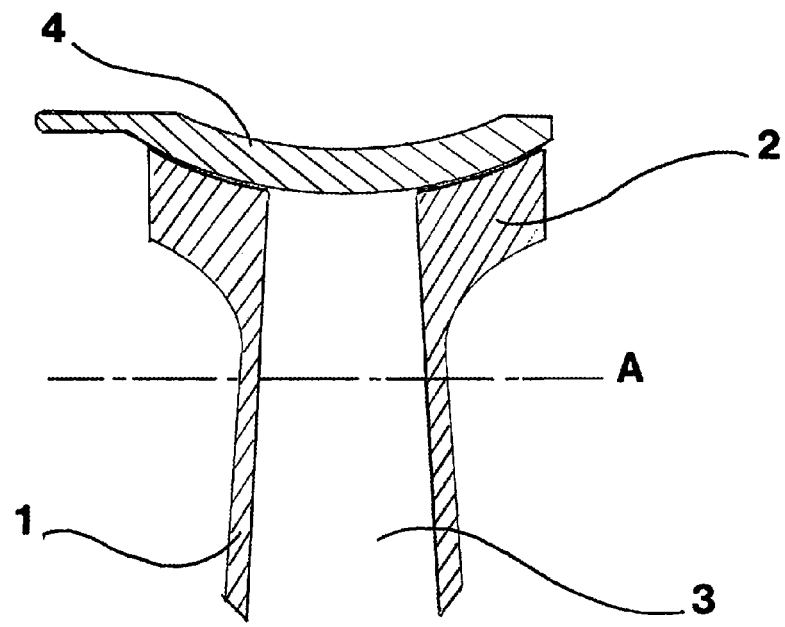
FIG. 2 is vertical sectional view of the sleeve and removable top flap seal.
Figure 2A:
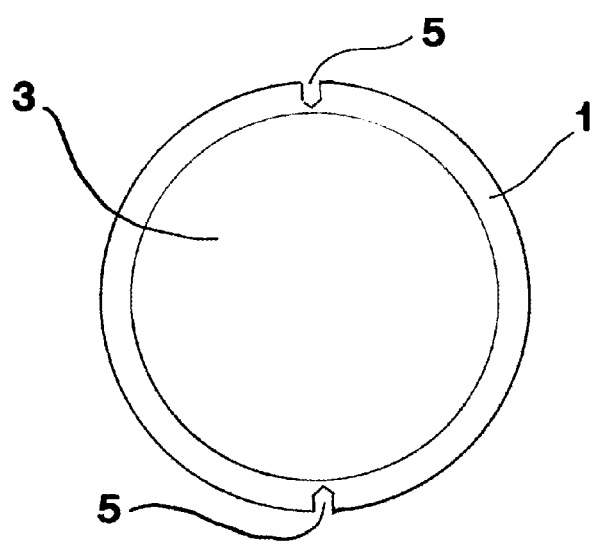
FIG. 2a is a horizontal cross section of the sleeve at level A.
Figure 3:
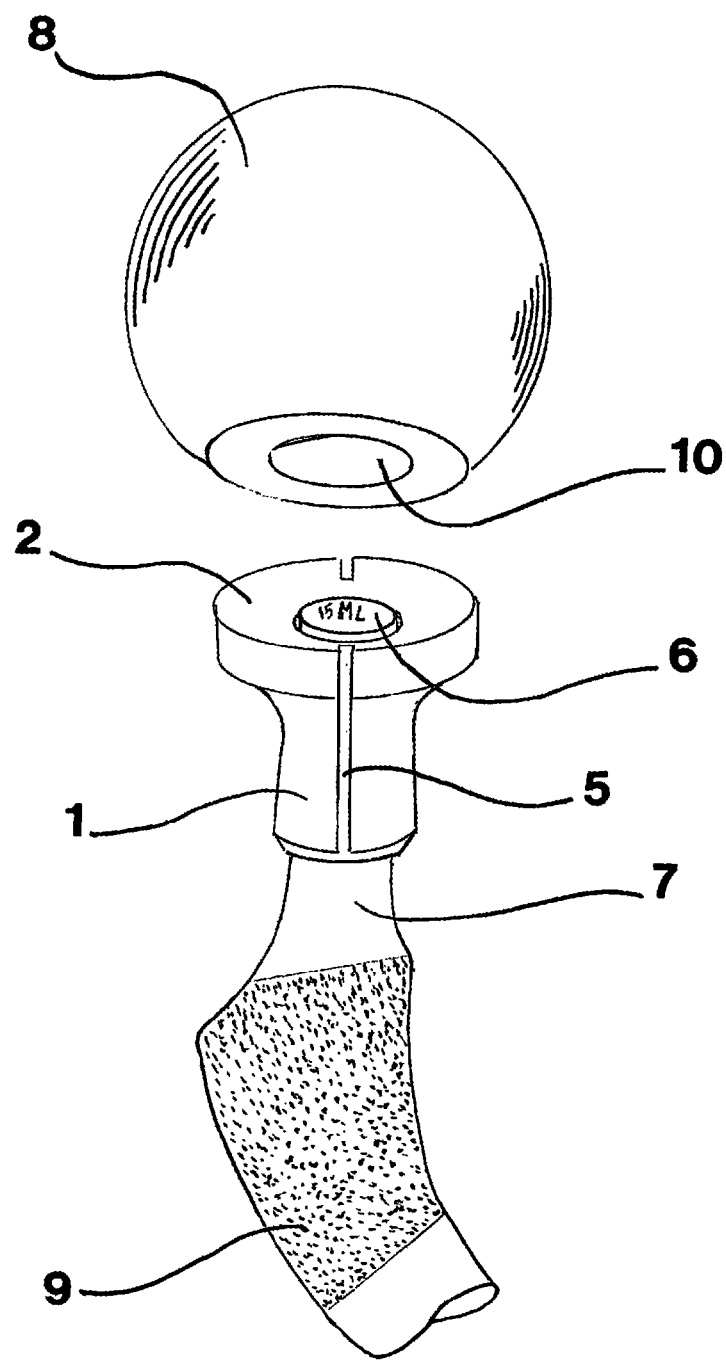
FIG. 3 is perspective view of the sleeve placed over the male Morse taper.
Figure 4:
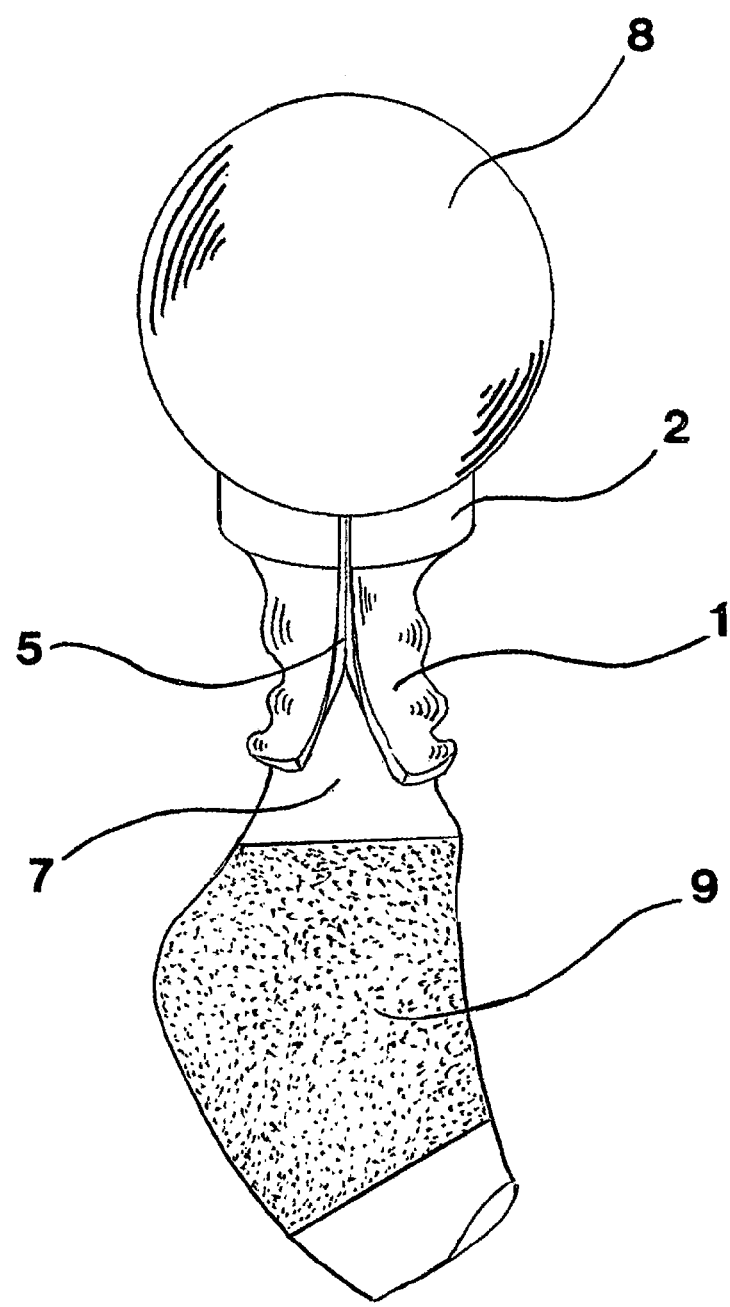
FIG. 4 is a perspective view of the protective sleeve being release during assembly.

A greater appreciation for an embodiment of the invention will be gained by reference to FIG. 1 wherein a conical sleeve 1 is shown in perspective having a circular rim 2 and a central channel 3. Furthermore, the outer surface of the protective sleeve provides a plurality of vertical release grooves 5 (see FIGS. 1 and 2a), which will split and spread wide open during the assembly as the female taper 10 of the articular ball 8 (see FIG. 3) is pushed down over the male taper 6 (see FIG. 4). The top surface of rim 2 may be flat or concave to better accommodate the curved surface of the articular ball 8 (see FIG. 4). A removable sealing cover flap 4 (see FIG. 2) is firmly attached to the top surface of rim 2 using contact adhesive. Said flap will keep the interior surface of the protective sleeve and the metallic surfaces of the taper free from any blood or other tissue contamination.

In use, the operating surgeon inserts the implant into appropriate position in the intended bone. The Morse taper of the implant is already covered by the protective sleeve, which remains in place during the surgical insertion process until the implant stem is fully seated. This keeps the Morse taper clean preventing contamination with blood, other bodily fluid and tissue particles. The operating surgeon will then peel off the sealing cover flap 4 exposing the top 6 of the male Morse taper. At this point, the operating surgeon will seat the articular ball 8 (see FIG. 3) over the rim 2 and insert the tip of the male Morse taper 6 over the female Morse taper 10 of the articular ball. The downward impaction of the articular ball during assembly will push the rim and protective sleeve slidingly distally toward the neck 7 (FIG. 4) of the implant. The larger diameter of the neck 7 will cause the protective sleeve to split open distally at the release grooves 5 and would be easily removed by the operating surgeon once the articular ball is completely seated.

There has thus been described a novel device aiming to protect the male Morse taper of an orthopedic implant during surgical insertion and eliminating risk of contamination of the contact surfaces by blood, bodily fluid and tissue particles present in the surgical wound and responsible for electrochemical bi-metal corrosion frequently requiring removal and revision of the implant.

What is claimed is:

1. A surgical device for providing protection against contamination of a taper contact surface with bodily fluid and tissue particles present in a surgical wound, the surgical device comprising:

an orthopedic implant having two portions, a first portion including a male Morse taper having the taper contact surface with a narrow top end and a larger bottom and a second portion including an articular ball having a female taper;

a splittable flexible conical hollow sleeve with a narrow top end and a splittable circular rim with a flat to surface, wherein the splittable circular rim has a larger outer diameter than the splittable flexible conical hollow sleeve and the splittable circular rim is firmly attached to an outer surface of the narrow to end of the splittable flexible conical hollow sleeve;

wherein the splittable flexible conical hollow sleeve prevents contamination of the orthopedic implant when the splittable flexible conical hollow sleeve is placed on the taper contact surface and the splittable circular rim forms a seal with the articular ball so that when a downward push is applied by the articular ball against the to flat surface of the splittable circular rim the splittable flexible conical hollow sleeve will split and start to slide downward thereby keeping the male Morse taper and the female taper sealed from bodily fluid contamination.

2. The surgical device of claim 1, wherein the outer surface of said splittable flexible conical hollow sleeve has a plurality of vertical grooves along its entire length.

3. The surgical device of claim 2, wherein said vertical grooves extend proximally into said splittable circular rim.

4. The surgical device of claim 1, wherein said splittable flexible conical hollow sleeve is constructed from a flexible extendable and malleable material including silicone, rubber or other soft and flexible polymers.

5. The surgical device of claim 1, wherein said splittable flexible conical hollow sleeve is a straight cylinder having the same length of taper contact surface.

6. The surgical device of claim 1, wherein said taper contact surface further comprises a thin metallic catalyst coating film which includes palladium.

7. The surgical device of claim 1, wherein the spittable flexible conical hollow sleeve is oval in shape.

8. The surgical device of claim 1, wherein the male Morse taper has an oval cross section.

9. The surgical device of claim 1, wherein the male Morse taper is covered by the splittable flexible conical hollow sleeve before any surgical insertion or manipulation.

* * * * *